(12) United States Patent
Glasky

(10) Patent No.: US 6,288,069 B1
(45) Date of Patent: Sep. 11, 2001

(54) USE OF 9-SUBSTITUTED HYPOXANTHINE DERIVATIVES TO STIMULATE REGENERATION OF NERVOUS TISSUE

(75) Inventor: Alvin J. Glasky, Tustin, CA (US)

(73) Assignee: NeoTherapeutics, Inc., Irvine, CA (US)

( * ) Notice: Subject to any disclaimer, the term of this patent is extended or adjusted under 35 U.S.C. 154(b) by 0 days.

(21) Appl. No.: 09/442,151

(22) Filed: Nov. 16, 1999

(51) Int. Cl.⁷ .................................................. A61K 31/52
(52) U.S. Cl. ............................................................ 514/262
(58) Field of Search .............................................. 514/262

(56) References Cited

U.S. PATENT DOCUMENTS

| | | | |
|---|---|---|---|
| 3,321,369 | 5/1967 | Glasky et al. | 167/65 |
| 3,438,486 | 4/1969 | Glasky | 260/211.5 |
| 3,666,856 | 5/1972 | Elion et al. | 424/180 |
| 4,035,486 | 7/1977 | Laborit | 424/178 |
| 4,221,909 | 9/1980 | Simon et al. | 544/265 |
| 4,340,726 | 7/1982 | Simon et al. | 536/17.4 |
| 4,643,992 | 2/1987 | Goodman et al. | 514/45 |
| 4,952,693 | 8/1990 | Sircar et al. | 544/255 |
| 5,023,294 | 6/1991 | Goto et al. | 524/547 |
| 5,091,432 | 2/1992 | Glasky | 514/262 |
| 5,093,318 | 3/1992 | Goodman et al. | 514/45 |
| 5,187,162 | 2/1993 | Marangos et al. | 514/46 |
| 5,237,051 | 8/1993 | Garbers et al. | 530/350 |
| 5,256,677 | 10/1993 | Sham et al. | 514/351 |
| 5,376,642 | 12/1994 | Yarchoan et al. | 514/45 |
| 5,447,939 | 9/1995 | Glasky et al. | 514/310 |
| 5,565,437 | 10/1996 | Marquez et al. | 514/45 |
| 5,595,901 | 1/1997 | Rocancourt et al. | 435/232 |
| 5,795,756 | 8/1998 | Johnson et al. | 435/183 |
| 5,801,159 | 9/1998 | Miller et al. | 514/45 |
| 5,801,184 | 9/1998 | Glasky et al. | 514/310 |
| 5,948,771 | 9/1999 | Danziger | 514/185 |
| 6,027,936 | 2/2000 | Glasky | 435/325 |

FOREIGN PATENT DOCUMENTS

| | | |
|---|---|---|
| WO 99/56550 | 11/1999 | (WO) . |
| WO 99/57119 | 11/1999 | (WO) . |
| WO 99/57120 | 11/1999 | (WO) . |

OTHER PUBLICATIONS

S. Lehmann et al., "Neurite Outgrowth of Neurons of Rat Dorsal Root Ganglia Induced by New Neurotrophic Substances with Guanidine Group," *Neurosci. Lett.* 152: 57–60 (1993).

M. Barinaga, "Carbon Monoxide: Killer to Brain Messenger in One Step," *Science* 259: 309 (1993).

A. Verma et al., "Carbon Monoxide: A Putative Neural Messenger," *Science* 259: 381–384 (1993).

M. Zuo et al., "Nitric Oxide and Carbon Monoxide Produce Activity–Dependent Long–Term Synaptic Enhancement in Hippocamus," *Science* 260: 1946–1950 (1993).

Å. Seiger et al., "Intracranial Infusion of Purified Nerve Growth Factor to an Alzheimer Patient: The First Attempt of a Possible Future Treatment Strategy," *Behavioural Brain Res.* 57: 255–261 (1993).

A. Nitta et al., "Effects of Oral Administration of a Stimulator for Nerve Growth Factor Synthesis in Basal Forebrain–Lesioned Rats," *Eur. J. Pharmacol.* 250: 23–30 (1993).

M.H. Tuszynski & F.H. Gage, "Neurotrophic Factors and Neuronal Loss" in *Alzheimer Disease* (R.D. Terry et al., eds., Raven Press, New York, 1994), ch. 25, pp. 405–417.

R.D. Hawkins et al., "Nitric Oxide and Carbon Monoxide as Possible Retrograde Messenges in Hippocampal Long–Term Potentiation," *J. Neurobiol.* 25: 652–665 (1994).

S.H. Snyder, "NO and CO: The Body's Unprecedented Signaling Molecules," *1995 Yearbook of Science and The Future, Encyclopedia Britannica*, pp. 84–101.

R.E. Callard & A.J.H. Gearing, "The Cytokine Facts Book" (Academic Press, London, 1994), pp. 99–100, 104–105, 120–123, 191–200, 235–236.

J.Z. Fields et al., "Cardiac Muscarinic Cholinergic Receptors: Biochemical Identification and Characterization," *J. Biol. Chem.* 253: 3251–3258 (1978).

D.H. Maurice & R.J. Haslam, "Molecular Basis of the Synergistic Inhibition of Platelet Function by Nitrovasodilators and Activators of Adenylate Cyclase: Inhibition of Cyclic AMP Breakdown by Cyclic GMP," *Mol. Pharmacol.* 37: 671–681 (1990).

I.D. Laviada et al., "Phosphatidylcholine–Phospholipase C Mediates the Induction of Nerve Growth Factor in Cultured Glial Cells," *FEBS Lett.* 364: 301–304 (1995).

A. Aurell et al., "The S–100 Protein in Cerebrospinal Fluid: A Simple ELISA Method," *J.Neurol. Sci.* 89: 157–164 (1989).

J. Barnett et al., "Human β Nerve Growth Factor Obtained from a Baculovirus Expression System Has Potent in Vitro and in Vivo Neurotrophic Activity," *Exp. Neurol.* 110:11–24 (1990).

(List continued on next page.)

*Primary Examiner*—Theodore J. Criares
*Assistant Examiner*—Jennifer Kim
(74) *Attorney, Agent, or Firm*—Oppenheimer Wolff & Donnelly LLP; Michael B. Farber

(57) ABSTRACT

The present invention comprises a method of stimulating regeneration or survival of a mammalian motor neuron or of a mammalian sensory neuron comprising administering to a mammal an effective amount of a compound that is a 9-substituted hypoxanthine derivative linked through a linker to a p-aminobenzoic acid moiety or of a salt or prodrug ester of such a compound. Preferably, the compound is N-4-carboxyphenyl-3-(6-oxohydropurin-9-yl) propanamide. The invention also includes pharmaceutical compositions formulated for stimulation of regeneration of a mammalian motor neuron comprising the 9-substituted hypoxanthine derivative and a pharmaceutically acceptable carrier.

12 Claims, 4 Drawing Sheets

OTHER PUBLICATIONS

A.J. Glasky et al., "Effect of AIT–082, a Purine Analog, on Working Memory in Normal and Aged Mice," *Pharm. Biochem. Behav.* 47: 325–329 (1994).

P.J. Middlemiss et al., "AIT–082, a Unique Purine Derivative, Enhances Nerve Growth Factor Mediated Neurite Outgrowth from PC12 Cells," *Neurosci. Lett.* 199: 131–134 (1995).

M.M. Bradford, "A Rapid and Sensitive Method for the Quantitation of Microgram Quantities of Protein Using the Principle of Protein–Dye Binding," *Anal. Biochem.* 72: 248–254 (1976).

K.L. Audus et al., "Brain Uptake of Drugs: the Influence of Chemical and Biological Factors," *Adv. Drug Res.* 23: 1–64 (1992).

W.A. Banks & A.J. Kastin, "Measurement of Transport of Cytokines Across the Blood–Brain Barrier," *Meth. Neurosci.* 16: 67–77 (1993).

A.L. Betz, "Identification of Hypoxanthine Transport and Xanthine Oxidase Activity in Brain Capillaries," *J. Neurochem.* 44: 574–579 (1985).

F.G. Blasberg et al., "Transport of α–Aminoisobutyric Acid Across Brain Capillary and Cellular Membranes," *J. Cereb. Blood Flow Metab.* 3: 8–32 (1983).

E.M. Cornford & W.H. Olendorf, "Independent Blood–Brain Barrier Transport Systems for Nucleic Acid Precursors," *Biochim. Biophys. Acta* 394: 211–219 (1975).

A.J. Glasky et al., "Neurotrophins, Growth Factorsand Mimetic Agents as Neuroprotectors in the Treatment of Alzheimer's Disease" in *Alzheimer Disease: From Molecular Biology to Therapy* (R. Becker & E. Giacobini, eds., Birkhäuser, Boston, 1996), pp. 119–124.

E.G. Gutierrez et al., "Murine Tumor Necrosis Factor Alpha Is Transported from Blood to Brain in the Mouse," *J. Neuroimmunol.* 47: 169–176 (1993).

M. Hosokawa & M. Ueno, "Aging of Blood–Brain Barrier and Neuronal Cells of Eye and Ear in SAM Mice," *Neurobiol. Aging* 20: 117–123 (1999).

M.D. Johnson & B.D. Anderson, "Localization of Purine Metabolizing Enzymes in Bovine Brain Microvessel Endothelial Cells: An Enzymatic Blood–Brain Barrier for Dideoxynucleosides?," *Pharm. Res.* 13: 1881–1886 (1996).

A.D. Mooradian, "Effect of Aging on the Blood–Brain Barrier," *Neurobiol. Aging* 9: 31–39 (1988).

W. Pan et al., "Permeability of the Blood–Brain Barrier to Neurotrophins," *Brain Res.* 788:87–94 (1998).

W.M. Pardridge, "CNS Drug Design Based on Principles of Blood–Brain Barrier Transport," *J. Neurochem.* 70: 1781–1792 (1998).

J.F. Poduslo et al., "Macromolecular Permeability Across the Blood–Nerve and Blood–Brain Barriers," *Proc. Natl. Acad. Sci. USA* 91: 5705–5709 (1994).

J.F. Poduslo & G.L. Curran, "Permeability at the Blood–Brain Barrier and Blood–Nerve Barriers of the Neurotrophic Factors: NGF, CNTF, NT–3, BDNF," *Mol. Brain Res.* 36: 280–286 (1996).

J.J. Ramirez et al., "AIT–082 Accelerates Septodentate Sprouting After Unilateral Entorhinal Cortex Lesion in Rats," *Soc. Neurosci. Abstr.* 24: 1942 (1998).

G.N. Shah & A.D. Mooradian, "Age–Related Changes in the Blood–Brain Barrier," *Exp. Gerontol.* 32: 501–519 (1997).

I. Skoog et al., "A Population Study on Blood–Brain Barrier Function in 85–Year–Olds: Relation to Alzheimer's Disease and Vascular Dementia," *Neurology* 50: 966–971 (1998).

R. Spector, "Hypoxanthine Transport Through the Blood–Brain Barrier," *Neurochem. Res.* 12: 791–796 (1987).

R. Spector, "Hypoxanthine Transport and Metabolism in the Central Nervous System," *J. Neurochem.* 50: 969–978 (1988).

D. Triguero et al., "Capillary Depletion Method for Quantitation of Blood–Brain Barrier Transport of Circulating Peptides and Plasma Proteins," *J. Neurochem.* 54: 1882–1888 (1990).

W.A. Banks et al., "Measurement of Efflux Rates from Brain to Blood" in *Methods in Molecular Biology, Neuropeptide Protocols* (G.B. Irvine & C.H. Williams, eds., Humana Press, Totowa, NJ, 1997), pp. 353–360.

W.A. Banks et al., "Effects of Wheatgerm Agglutinin and Aging on the Regional Brain Uptake of HIV–1 gp120," *Life Sci.* 65: 81–89 (1999).

M.P. Rathbone et al., "Physiology and Pharmacology of Natural and Synthetic Nonadenine–Based Purines in the Nervous System," *Drug Dev. Res.* 45: 356–372 (1998).

M.P. Rathbone et al., "AIT–082 as a Potential Neuroprotective and Regenerative Agent in Stroke and Central Nervous System Injury," *Exp. Opin. Invest. Drugs* 8: 1255–1262 (1999).

J.S. Bintner et al., "AIT–082, a Hypoxanthine Derivative, Prevents Much of the Decrease in Cerebellar Neuron ATP Following Glutamate Exposure," *Soc. Neurosci.* 25: 2131 (1999) (abstract).

R. Huang et al., "Enhancement of Neuronal Cell Excitability by AIT–082 in Rat Hippocampal Neurons and Its Effects on Second Messenger Systems," *Soc. Neurosci.* 24: 1941 (1998) (abstract).

O.Chu–LaGraff et al., "Effect of AIT–082 on Brain NGF mRNA Levels and Transport of AIT–082 Across the Blood–Brain Barrier," *Soc. Neurosci.* 24: 1941 (1998) (abstract).

F. Caciagli et al., "The Hypoxanthine Derivative AIT–082 Protects Against Neurotoxicity in Vitro and in Vivo," *Soc. Neurosci.* 24: 1941 (1998) (abstract).

B.H.J. Juurlink et al., "The Hypoxanthine Analogue AIT–082 Promotes Neurite Formation and Regeneration in Cultured Hippocampal Neurons," *Soc. Neurosci.* 24: 1941 (1998) (abstract).

E.M. Taylor et al., "$^{14}$C–AIT082 Crosses the Blood–Brain Barrier and Is Pumped Out of Brain by a Probenecid– and Verapamil–Sensitive Mechanism," *Soc. Neurosci.* 25: 1758 (1999) (abstract).

F. Caciagli et al., "The Hypoxanthine Analogue AIT–082 Mimics the Activity of Guanosine in Affecting Extracellular Adenosine Breakdown and Glutamate Reuptake in Rat Cultured Astrocytes," *Soc. Neurosci.* 25: 1195 (1999) (abstract).

R. Ciccarelli et al., "Guanosine and Related Drugs Stimulate the Production of Neurotrophic Factors from Rat Cultured Astrocytes by Involving Mitogen–Activated Protein Kinase Pathway," *Soc. Neurosci.* 25: 1013 (1999) (abstract).

P.J. Middlemiss et al., "The Synthetic Purine AIT–082 Enhances Recovery After Acute Spinal Cord Crush Injury in Rats," *Soc. Neurosci.* 25: 1002 (1999) (abstract).

P. Di Iorio et al., "The Hypoxanthine Derivative AIT–082 Is Protective Against NMDA– or Kainic Acid–Induced Rate Hippocampal Neurotoxicity in Vivo," *Soc. Neurosci.* 25: 756 (1999) (abstract).

A.G. Gittis & J.R. Puzuasky, "AIT–082 Improves Memory Performance in a Non–Match–to–Sample Task in Rats," *Soc. Neurosci.* 25: 62 (1999) (abstract).

USE OF 9-SUBSTITUTED HYPOXANTHINE DERIVATIVES TO STIMULATE REGENERATION OF NERVOUS TISSUE

FIELD OF THE INVENTION

The present invention is directed to use of multifunctional pharmaceutical compounds possessing unique and unexpected combinations of biological activities. In particular, the present invention is directed to use of such compounds to stimulate regeneration of mammalian motor nerve tissue.

BACKGROUND OF THE INVENTION

The modification of pharmaceutical and biologically active compounds to alter or enhance their functional properties is known in the art. Typically, prior art efforts have been directed to the production of carrier-bound drugs in which carrier molecules having selective physical properties, such as enhanced water solubility, are chemically attached to biologically active compounds. For example, Jacobson and colleagues have developed what is referred to as the "functional congener" approach to the design of carrier-bound drugs (Jacobson, K. A., in *Adenosine Receptors*; Cooper, D. M. F., Londos, C., Eds., *Receptor Biochemistry and Methodology*; Venter, J. C., Harrison, L. C., Eds., Alan, R., Liss: New York, 1988, Vol. 11, pp. 1–26). This approach involved the modification of well-defined drug molecules at non-sensitive positions in a manner that retained the drug's ability to bind at its specific receptor site. In order to produce a chemically functionalized drug congener, they modified the drug molecule by the introduction of a chemical functional group which could then be covalently attached to a carrier molecule. This produced a bifunctional molecule in which one portion (the "pharmacophore") contributed its biological activity, and the second portion, or carrier, imparted its selective physical properties such as enhanced receptor attachment or water solubility. Using this approach, functional congener compounds were prepared using catecholamines, adenosine receptor agonists and antagonists, and muscarinic agents.

However, recent developments in the understanding of biological mechanisms such as the binding of selective ligands to receptors and their related functions and such seemingly diverse physiological systems as the cardiovascular system, the central nervous system, and the immune system has stimulated efforts to discover alternative methods for designing biologically active compounds exhibiting properties which will selectively treat or regulate such seemingly diverse physiological systems without serious or disabling side effects that might otherwise occur. For example, adenosine receptors have been found in the cardiovascular system, the central nervous system, and the immune system. Accordingly, it was originally believed that the development of adenosine analogues would be effective in regulating or modifying the biological activities associated therewith. However, the ubiquitous distribution of adenosine receptors has resulted in the production of serious and disabling side effects in what were originally believed to be unrelated biological systems, thereby significantly reducing the therapeutic usefulness of adenosine analogues.

Similar interrelationships have also been discovered to exist between the mammalian immune system and the mammalian nervous system. Over the past several decades numerous researchers have added considerable detail to the overall understanding of the mammalian immune system and its importance in maintaining overall physical health. In more recent years, similar detail has evolved in the study of the nervous system. As more and more information was developed in the seemingly independent fields of study, a number of close functional parallels began to appear between the two physiological systems. For example, both systems are concerned with the storage of information and use soluble chemicals to transmit signals between cells. Additionally, natural endogenous substances, such as hormones and transmitters, are active on the cells of both systems. Even more significantly, some common functions between the two systems are based upon similar chemical structures or markers on the surfaces of both nerve cells and immune cells. The recent discovery that the CD4 receptors targeted by the AIDS virus are present on both the T4 lymphocyte and on neurons is one of the more dramatic examples of the close relationship between the nervous system and the immune system.

Further crossing the classically imposed barriers between the fields of immunology and neurology, recent developments in the understanding of Alzheimer's disease have implicated an immunologic component that may be present in this neurological disorder. It has been proposed that both the anatomical and biochemical specificity of the defects seen in Alzheimer's disease could be explained by an immunologic attack on the brain blood vessels themselves with secondary involvement of neuronal, glial, or synaptic constituents contributing to the formation of senile plaques, or an immune-mediated compromise of vessels associated with an immune attack on specific neuronal, glial, or synaptic constituents (Appel, S. H., Neurobiol. Aging, 7:512, 1986).

Additionally, circumstantial evidence for any immunological component in neurologic disorders is also provided by the altered suppressor cell function and aging populations, and more specifically in Alzheimer's disease (MacDonald et al., Clin. Exp. Immunol. 49:123–8, 1982; Miller, A. E., Ann. Neurol. 10:506–10, 1981; Stefansson, K. in *Clinical Neurology of Aging*, Ed. M. L. Albert, Oxford Univ. Press, 1984, pp. 76–94), the implication of HLA regions of chromosome 6 and the GM locus chromosome 14 in a large kindred with Alzheimer's disease (Weitkamp, L. R., Am. J. Hum. Genet. 35:443–53, 1983) and by the altered immunological parameters in Down's syndrome, a disease whose symptoms are similar to senile dementia of the Alzheimer's type (SDAT).

Scientists in the nascent field of neuroimmunology have hypothesized the effects and the function of brain cells (neurons) may be observed concomitantly as parallel defects or deficiencies in receptors on the cells of the immune system (such as peripheral blood immune cells). The validity of this hypothesis was recently brought to light with the aforementioned discovery of HIV infection in neurons. This neuroimmunologic theory has had significant impact because formerly almost all neuropsychiatric disorders were thought to be primarily due to factors such as genetic predisposition, mental attitude, and/or resistance to natural environment rather than defects or deficiencies in cell function. Similarly, though the immune system has been implicated in numerous diseases resulting from infection and cancer to degenerate diseases such as Alzheimer's disease, arthritis and aging, its relationship to cognitive functioning was previously unrealized.

Because the chemical interrelationship between these diverse physiological systems has been recognized only recently, prior art medical treatments and pharmaceutical agents have focused almost exclusively on treating the individual systems alone. Thus, pharmaceutical compounds have been developed for treating or regulating the cardiovascular system or the immune system or the central nervous system with the idea of avoiding undesirable interactions in what are now known to be related physiological systems. By far the greatest amount of recent effort in the pharmaceutical and medical fields has been devoted to the treatment and regulation of the immune system alone. Numerous immunomodulating and antiviral agents have been disclosed in the art such as those described in European Patent Application Publication No. 0126813 (Simon et al.), U.S. Pat. No. 4,221,909 (Simon et al.), U.S. Pat. No. 4, 211, 794 (Kraska), and U.S. Pat. No. 4,221,910 (Giner-Sorolla). Unlike antibiotics which directly attack or destroy invading organisms such as bacteria, immunomodulating agents and more specifically immune enhancing agents are compounds which help to bolster the body's own defense mechanisms against the effects of infections. Immunomodulators either restore depressed immune function, or suppress hyperactive immune function.

Though the AIDS epidemic has focused considerable resources and attention to the study of defects and deficiencies in the immune system, outside of the recent discovery of HIV infection in neural tissue, comparatively little research has been directed to the development of multifunctional pharmaceutical compounds such as neuroimmunologic agents or other compounds exhibiting functionally related and mutually supportive therapeutic activities such as immunomodulating with cardiovascularly active compounds or immunomodulating with antimicrobially active compounds.

One of the aspects of neurodegenerative diseases such as Alzheimer's disease, amyotrophic lateral sclerosis (ALS or Lou Gehrig's disease), Parkinson's disease, and other similar diseases and conditions is the occurrence of the death of nerve cells, particularly motor neurons. Similar death occurs after injuries such as spinal cord injuries. More than 100,000 Americans are estimated to sustain spinal cord injuries each year. The final outcomes of these injuries are not only determined by the mechanical trauma but also by the subsequent cellular and molecular events which constitute the secondary injury. Conventional therapy is generally aimed at reducing the initial inflammatory response and edema to lessen secondary damage. More recently, physicians and researchers have strived to promote regeneration of severed connections.

Neurotrophic factors have been shown to play a role in the regeneration of spinal cord motor neurons in vitro (V. M. K. Verge et al., *Phil. Trans. Roy. Soc. B.* 351: 423–430 (1996)). Although attempts have been made to reverse this cell death and promote regeneration of motor neurons by the administration of nerve growth factors, such efforts are complicated by the existence of the blood-brain barrier. The difficulty in the use of neurotrophic factors themselves as therapeutic agents lies in the delivery of the large protein molecules to the spinal cord. Oral delivery is not possible for proteins owing to the activity of proteases in the digestive tract and neurotrophic factors are too large to pass through the blood-brain barrier after injection. Clinical trials with one neurotrophic factor, CNTF, demonstrated the significant side effects associated with systemic delivery (ALS CNTF Treatment Study Group, *Neurology* 46: 1244–1249 (1996)).

A novel approach to neurotrophic factor therapy involves transplanting cells transfected with neurotrophic factor genes directly into the spinal cord lesion. This approach also has several drawbacks. Generally, each group of transplanted cells produces only one neurotrophic factor and studies to date suggest that a combination of factors may be required for a successful regenerative response (R. Grill et al., *J. Neurosci.* 17: 5560–5572 (1997)). In addition, this is an invasive treatment which may present adverse responses including inflammatory responses, localized hyperplasia, and uncertain levels of neurotrophic factor production. Similar and additional concerns arise with delivery of neurotrophic factors directly into the cerebrospinal fluid (E. F. Fernandez et al., *Neurosurgery* 33: 889–893 (1993)). A small orally-absorbed molecule, which passes the blood-brain barrier and which stimulates the appropriate neurotrophic factor production at the required location, would be preferable.

Therefore, there is a requirement for improved methods of administering compounds that can stimulate the activity of nerve growth factors and enable the regeneration of motor neurons to restore functioning of the central nervous system in such conditions. There is a particular need to do so using compounds and compositions that selectively pass through the blood-brain barrier.

Accordingly, it is a principal object of the present invention to disclose multifunctional pharmaceutical compounds possessing at least two separate pharmacological activities that are functionally related and mutually supportive therapeutically.

It is an additional object of the present invention to provide multifunctional pharmaceutical compounds pairing biologically active chemical moieties such as immunomodulating pharmacophores, neurological pharmacophores, cardiovascular pharmacophores and anti-microbial pharmacophores as well as others.

It is a further object of the present invention to provide multifunctional pharmaceutical compounds combining biologically active chemical moieties which produce a combined pharmacological activity differing in either or both quantity or character from the individual pharmacological actions of the separate chemical moieties. It is a further additional object of the present invention to disclose specific neurologically active immunomodulating compounds that are pharmaceutically active with respect to defects or deficiencies, into both the central nervous system and the immune system. These particular compounds will be especially effective for treating neuroimmunologic conditions such as Alzheimer's disease, AIDS, disorders of memory, and disorders of immune function, as well as the effects of aging.

It is a further object of the invention to provide improved methods for stimulating nerve growth in neurodegenerative conditions such as Alzheimer's disease, ALS Parkinson's disease and other similar conditions by using reagents that selectively pass through the bloodbrain barrier.

SUMMARY

The present invention encompasses the use of 9-substituted hypoxanthine derivatives to stimulate regeneration of mammalian motor neurons and mammalian sensory neurons. The 9-substituted hypoxanthine derivatives pass through the blood-brain barrier and provide an alternative to the injection of reagents directly into the nervous system.

One embodiment of the present invention is a method of stimulating regeneration of a mammalian motor neuron or sensory neuron comprising administering to a mammal an effective amount of a compound of formula

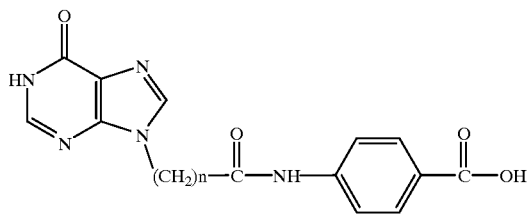

where n is an integer from 1 to 6 or of a salt or a prodrug ester of a compound of formula (I) where n is an integer from 1 to 6.

Preferably, n is 2; where n is 2, the compound is N-4-carboxyphenyl-3-(6-oxohydropurin-9-yl) propanamide.

The administration of N-4-carboxyphenyl-3-(6-oxohydropurin-9-yl) propanamide can increase the level of mRNA of at least one neurotrophic factor in a tissue that is in chemical communication with the motor neuron or the sensory neuron, the neurotrophic factor stimulating the growth of neurons. The neurotrophic factor can be nerve growth factor, NT-3, brain-derived neurotrophic factor (BDNF), or ciliary neurotrophic factor (CNTF) or other neurotrophic factors which may be involved in sensory or motor neuron survival or regeneration.

Another aspect of the present invention is a pharmaceutical composition comprising:

(1) an effective amount of a compound of formula (I); and
(2) a pharmaceutically acceptable carrier.

As described above, n is an integer from 1–6. The composition is formulated for stimulation of regeneration of a mammalian sensory or motor neuron.

Preferably, in the composition, n is 2 and the compound is N-4-carboxyphenyl-3-(6-oxohydropurin-9-yl) propanamide.

BRIEF DESCRIPTION OF THE DRAWINGS

The following invention will become better understood with reference to the specification, appended claims, and accompanying drawings, where:

DESCRIPTION

Figure 1:
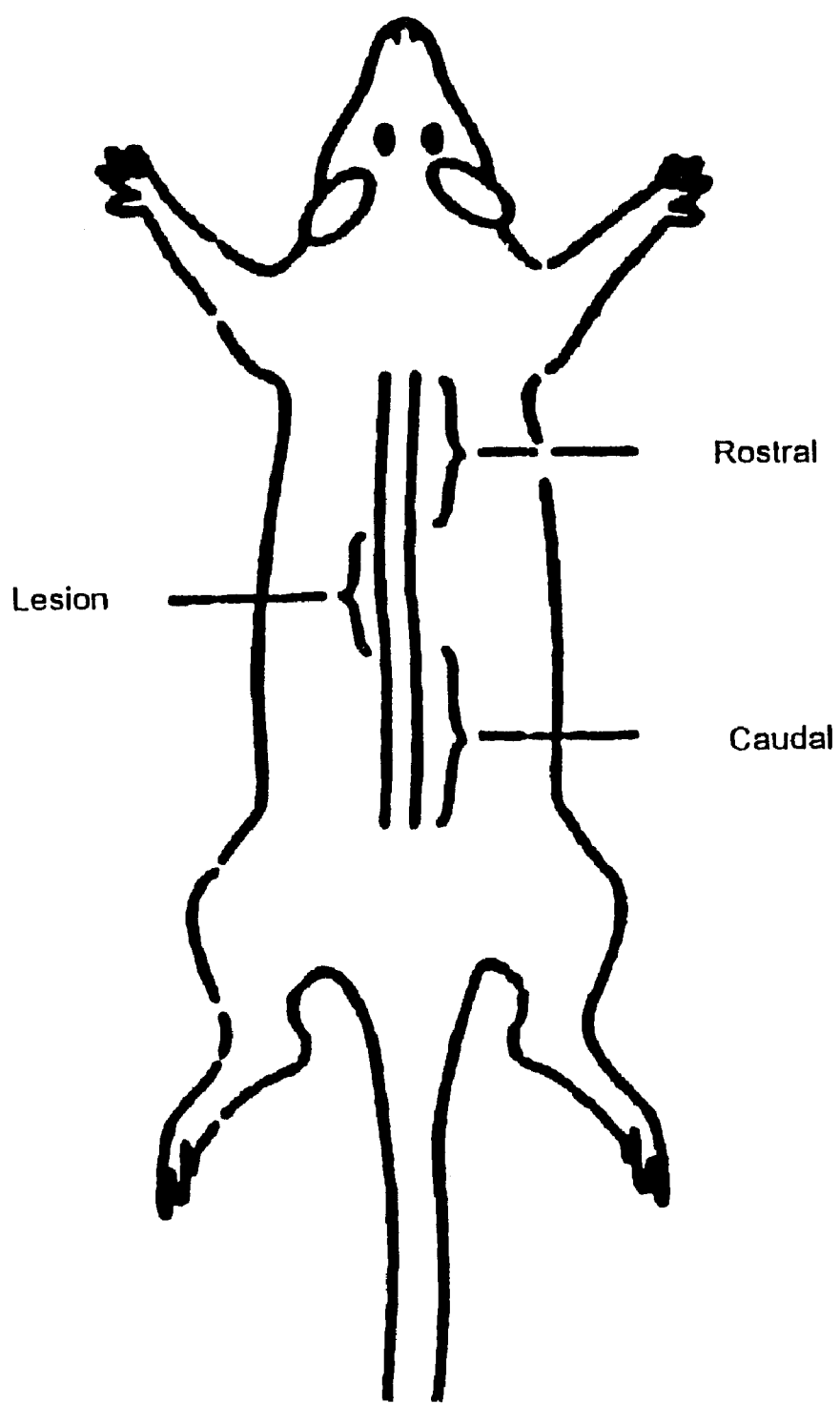
FIG. 1 is a diagram of the location of the lesions made in the spinal cord of rats to which a 9-substituted hypoxanthine derivative, N-4-carboxyphenyl-3-(6-oxohydropurin-9-yl) propanamide, was administered in Example 1.

Unexpectedly, it has been found that 9-substituted hypoxanthine derivatives, particularly compounds in which hypoxanthine and p-aminobenzoic acid (PABA) are linked through a hydrocarbon linker containing an amide group can stimulate regeneration of mammalian motor neurons. Unexpectedly, it has been found that the administration of such compounds can stimulate the activity of one or more neurotrophic factors and thereby help to bring about regeneration of motor neurons.

In general, the present invention comprises a method of stimulating regeneration of a mammalian motor neuron comprising administering to a mammal an effective amount of a compound of formula (I) where n is an integer from 1 to 6 or of a salt or prodrug ester of a compound of formula (I) where n is an integer from 1 to 6.

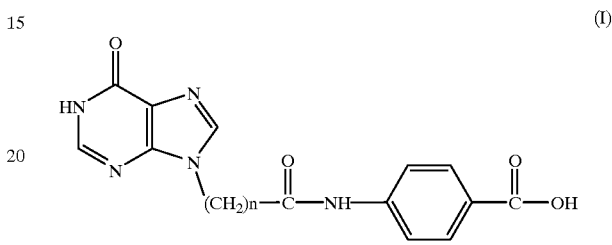

Preferably, n is 2; when n is 2, the compound is N-carboxyphenyl-3-(6-oxohydropurin-9-yl) propanamide.

More specifically, the present invention involves the use of a purine analogue, N-carboxyphenyl-3-(6-oxohydropurin-9-yl) propanamide, which, in a broad aspect, can be viewed as analogous to hypoxanthine chemically linked to a p-aminobenzoic acid analogue. Surprisingly, this compound exhibits functional features of both hypoxanthine and p-aminobenzoic acid as well as functions not provided by either substance as a single entity. As a result, it is able to pass through the blood-brain barrier following oral administration or administration through injection into the bloodstream and, because of the structural similarity of a portion of this compound to p-aminobenzoic acid, it exhibits physiological activity mimicking p-aminobenzoic acid. Thus, it can function as an orally administered or injectable treatment for conditions in which motor neurons have been destroyed as the result of trauma, disease, or chemical or biological insult. Exemplary dosages in accordance with the teachings of the present invention range from 0.01 mg/kg to 60 mg/kg, though alternative dosages are contemplated as being within the scope of the present invention.

Suitable dosages can be chosen by the treating physician by taking into account such factors as the size, weight, age, and sex of the patient, the physiological state of the patient, the severity of the condition for which the compound is being administered, the response to treatment, the type and quantity of other medications being given to the patient that might interact with the compound, either potentiating it or inhibiting it, and other pharmacokinetic considerations such as liver and kidney function.

As shown below in the Examples, the administration of N-4-carboxyphenyl-3-(6-oxohydropurin-9-yl) propanamide increases the level of mRNA encoding at least one neurotrophic factor in a tissue that is in chemical communication with the motor neuron. The neurotrophic factor stimulates the growth of neurons.

The neurotrophic factor can be one of nerve growth factor, NT-3, brain-derived neurotrophic factor (BDNF), and ciliary neurotrophic factor (CNTF) or any other neurotrophic factors which may be involved in motor or sensory neuron survival or regeneration.

Functional nerve growth factor is a non-covalently linked parallel homodimer. The structure of nerve growth factor consists of three anti-parallel pairs of β-strands together forming a flat surface through which the two subunits associate.

The amino acid sequence for human nerve growth factor and mouse nerve growth factor is known. This molecule is described in R. E. Callard & A. J. H. Gearing, "The Cytokine Facts Book" (Academic Press, London, 1994), pp. 191–198, incorporated herein by this reference.

The growth factor NT-3 also promotes the survival and outgrowth of neural crest-derived sensory and sympathetic neurons. The structure of this molecule is known; its amino acid sequence is identical in the human and mouse. The structure has 60% β-sheet secondary structure and exists as a tightly linked homodimer. NT-3 is described in R. E. Callard & A. J. H. Gearing, "The Cytokine Facts Book" (Academic Press, London, 1994), pp. 199–200, incorporated herein by this reference.

Brain derived neurotrophic factor also promotes the survival of neuronal populations located either in the central nervous system or directly connected to it. It helps to maintain neurons and their differentiated phenotype in the adult. The amino acid sequence is known for human and mouse BDNF. The molecule has 70% β-sheet secondary structure and is expressed as a tightly associated homodimer. Properties of this molecule are described in R. E. Callard & A. J. H. Gearing, "The Cytokine Facts Book" (Academic Press, London, 1994), pp. 99–100, incorporated herein by this reference.

Ciliary neurotrophic factor also promotes the survival and/or differentiation of neuronal cells. CNTF has no homology with NGF, BDNF, and NT-3. The absence of a signal peptide in N-linked glycosylation sites in CNTF is consistent with its being a cytosolic protein. The three-dimensional structure of CNTF is not known, but it has significant homologies with other cytokines, such as IL-6, LIF, oncostatin M, and G-CF. It is thought that these molecules share a four-helix bundle structure. The amino acid sequences of human CNTF and rat CNTF are known. Although these sequences are similar, they are not identical. Further information about CNTF is given at R. E. Callard & A. J. H. Gearing, "The Cytokine Facts Book" (Academic Press, London, 1994), pp. 104–105, incorporated herein by this reference.

Although Applicant does not intend to be bound by this theory, the increase of the level of mRNA of these neurotrophic factors brought about by the methods of the present invention is believed to promote neuronal survival.

The term "effective amount" as used herein in the specification means an amount of the compound that causes a detectable increase in the messenger RNA level of at least one of the recited neurotrophic factors. Methods of measuring the mRNA levels are described further in the Examples and are generally known in the art; such methods typically involve hybridization to probes containing mRNA-specific sequences and detecting the quantity of hybrid nucleic acid formed. The hybrid nucleic acid formed is typically detected by a label incorporated in one of the two nucleic acid strands forming the hybrid. This label can be radioactive or non-radioactive; if non-radioactive it can be fluorescent, chemiluminescent, bioluminescent, enzymatic, or can make use of another detectable property. Detection can also be performed using the polymerase chain reaction (PCR) mechanism or a variant thereof. PCR is described in detail in U.S. Pat. No. 4,683,195 to Mullis et al. and U.S. Pat. No. 4,683,202 to Mullis et al. Other detection methods, including other amplification methods, are known in the art.

Another aspect of the present invention is a pharmaceutical composition. The pharmaceutical composition comprises: (1) an effective amount of a compound of formula (I) as described above; and (2) a pharmaceutically acceptable carrier. The pharmaceutically acceptable carrier can be chosen from those generally known in the art, including, but not limited to, human serum albumin, ion exchangers, alumina, lecithin, buffered substances such as phosphate, glycine, sorbic acid, potassium sorbate, and salts or electrolytes such as protamine sulfate. Other carriers can be used.

The composition is formulated for stimulation of regeneration or survival of a mammalian sensory neuron or a mammalian motor neuron.

Methods for synthesis of suitable compounds for use in methods according to the present invention are described, for example, in U.S. Pat. No. 5,091,432 to Glasky, incorporated herein by this reference. In general, such methods comprise the steps of: (1) synthesis of an appropriately substituted purine moiety with a 6-amino group linked to an aliphatic linker in which the linker is terminated with a carboxyl group protected such as with an alkyl ester; (2) converting the 6-amino group to a 6-oxo group by oxidation, such as with sodium nitrite; (3) hydrolyzing the alkyl ester (or other analogous protecting group) to yield a carboxylic acid; (4) activating the free carboxylic acid by converting it to a nitrophenyl ester; (5) reacting the nitrophenyl ester with a p-aminobenzoate moiety protected with an ethyl ester; and (6) hydrolyzing the ethyl ester protecting the p-aminobenzoate moiety to produce the final product. This sequence of reactions is exemplified in Examples 1–6 for the synthesis of N-4-carboxyphenyl-3-(6-oxohydropurin-9-yl) propanamide. The length of the aliphatic linker covalently bound to the purine moiety can be varied to vary the distance between the hypoxanthine and p-aminobenzoate moieties. Other synthetic routes can be used and are known in the art.

The invention is illustrated by the following Examples. These Examples are presented for illustration only and are not intended to limit the invention.

EXAMPLE 1

SYNTHESIS OF 3-(1,6-DIHYDRO-6-AMINO-9H-PURIN-9-YL) PROPIONIC ACID, ETHYL ESTER

Adenine (10.0 g, 74.00 mmol) was placed into a clean, dry, 500 ml round bottom flask equipped with a magnetic stirring bar, reflux condenser, and a $CaC_2$ drying tube. Absolute ethanol (360 ml) was added and the solution was stirred. To the suspension was added a small piece of sodium (approximately 75 mg); when the sodium had completely reacted, 22.2 g (0.222 mmol) ethyl acrylate was added to the suspension and the mixture was brought to reflux. Reflux was continued overnight for approximately 18 hours and the resulting lime colored homogeneous solution was allowed to cool slowly to room temperature. Crystals were allowed to form at 4° C. The solution was filtered by Buchner vacuum filtration and the solid was washed with anhydrous ether. Upon drying, 15.2 g (64.6 mmol) of 3-(1,6-dihydro-6-amino-9 H-purin-9-yl) propionic acid, ethyl ester was obtained. The yield was 87%, and the melting point was 166°–167° C.

EXAMPLE 2

SYNTHESIS OF 3-(1,6-DIHYDRO-6-OXO-9 H-PURIN-9-YL) PROPIONIC ACID, ETHYL ESTER

The compound synthesized in Example 1,3-(1,6-dihydro-6-amino-9H-purin-9-yl) propionic acid, ethyl ester (15.2 g, 64.6 mmol) was placed into a 500 ml round bottom flask with 350 ml glacial acetic acid and was stirred to complete the dissolution. While the solution was being stirred, 22.3 g (0.323 mmol) NaNO$_2$ dissolved in water (saturated) was added dropwise over a period of 1 hour using a dropping funnel (pressure equalizing). A brown gas formed during the addition. The flask was stopped shortly after the addition was complete and the solution was stirred at room temperature for 24 hours. The solvent was removed under reduced pressure (approximately 45°–50° C. The residue was washed with cold (0° C.) absolute ethanol and filtered. The resulting white solid was dissolved in 175 ml ethanol/water (70/30) and was cooled to 0° C. overnight. The resulting precipitate was obtained by filtration. The solid was placed into a flask with a magnetic stirring bar and was washed with water by vigorous stirring. The solution was filtered by Buchner vacuum filtration and the resulting white solid was dried in vacuo at 50° C. to yield 4.6 g (19.5 mmol) of 3-(1,6-dihydro-6-oxo-9 H-purin-9-yl) propion acid, ethyl ester. The yield was 30% and the melting point was 197°–200° C.

EXAMPLE 3

SYNTHESIS OF 3-(1,6-DIHYDRO-6-OXO-9H-PURIN-9-YL) PROPANOIC ACID

The product from Example 2,3-(1, 6-dihydro-6-oxo-9H-purin-9-yl) propanoic acid, ethyl ester (20.00 g, 84.66 mmol) was placed into a 500 ml round bottom flask equipped with a magnetic stirring bar. Water (150 ml) was added to the flask of the solution stirred. To the stirring heterogeneous solution was added 10.4 g (0.1854 mmol) of KOH pellets. Within a few minutes the solution became a homogenous light green color. The solution was stirred at room temperature for 3.5 hours. The solution was acidified (pH approximately 1.0) with concentrated HCl. The precipitated solution was placed at 4° C. overnight. The solid was collected by filtration, washed sequentially with water, methanol, and ether, and dried. The product, 3-(1,6-dihydro-6-oxo-9 H-purin-9-yl) propanoic acid (17.63 g; 84.7 mmol) was obtained as a free flowing white solid. The yield was 100%.

EXAMPLE 4

SYNTHESIS OF 3-(1,6-DIHYDRO-6-OXO-9H-PURIN-9-YL) PROPANOIC ACID, 4-NITROPHENYL ESTER

The product from Example 3, 3-(1, 6-dihydro-6-oxo-9H-purin-9-yl) propanoic acid (7.00 g; 0.03363 mmol) was added to a 250 ml round bottom flask equipped with a magnetic stirring bar. Anhydrous pyridine was added and the solution was stirred. To the resulting heterogeneous solution was added 11.46 g (0.04876 mmol) of 4-nitrophenyl trifluoromethyl acetate under a stream of nitrogen. The solution was stirred at 30° C. for 17 hours. The resulting thick slurry was cooled to room temperature and 175 ml of distilled H$_2$O was added to the stirring solution. The solution became homogeneous and then a precipitate formed. The mixture was placed in the freezer for several hours (less than 0° C.). The solution was removed from the freezer and was allowed to thaw. The solid was collected by filtration and was washed with H$_2$O, methanol, and ether. Upon drying, 10.32 g of 3-(1,6-dihydro-6-oxo-9H-purin-9-yl) propanoic acid, 4-nitrophenyl ester as a white solid was obtained. The yield was 93%.

EXAMPLE 5

SYNTHESIS OF 4-[[3-(16-DIHYDRO-6-OXO-9H-PURIN-9-YL)-1-OXYPROPYL-] AMINO] BENZOIC ACID ETHYL ESTER

The product of Example 4, 3-(1,6-dihydro-6-oxo-9H-purin-9-yl) propanoic acid, 4-nitrophenyl ester (165 mg, 0.50 mmol) and 84 mg (0.50 mmol) of 4-aminobenzoic acid ethyl ester were heated together in 1.5 ml of dimethyl sulfoxide at 35° C.-40° C. for 72 hours. A white precipitate was observed at the bottom of the flask. Acetone (10 ml) was added and the solid was collected by Buchner vacuum filtration. The solid was washed twice with acetone and was allowed to dry. This yielded 53 mg of 4-[[3-(1,6-dihydro-6-oxo-9H-purin-9-yl)-1-oxopropyl-] amino] benzoic acid, ethyl ester as a white solid. The melting point was 265° C.–269° C. The yield was 30%.

EXAMPLE 6

SYNTHESIS OF N-4-CARBOXYPHENYL-3-6-OXOHYDROPURIN-9-YL) PROPANAMIDE

The product of the synthesis of Example 5, 4-[[3-(1,6-dihydro-6-oxo-9H-purin-9-yl)-1-oxopropyl] amino] benzoic acid, ethyl ester (8.88 g; 24.99 mmol) was placed into a 500 ml round bottom flask with 180 ml water and a magnetic stirring bar. To the stirring solution, 135 ml of a 0.53 molar KOH (aq.) solution was added dropwise over a period of 1 hour. The solution was stirred at room temperature for 3.5 hours. The solution was brought to approximately pH 3.0 with dilute HCl and was then vacuum filtered. The resulting fine white solid was washed with water and subsequently with methanol. Upon drying under vacuum at approximately 45° C., 7.34 g (22.4 mmol) of a white solid, N-4-carboxyphenyl-3 (6-oxohydropurin-9-yl) propanamide or 4-[[3-(1,6-dihydro-6-oxo-9H-purin-9-yl)-1-oxopropyl-] amino] benzoic acid was obtain The melting point was 319° C.–321° C. The yield was 90%.

EXAMPLE 7

EFFECT OF N-4-CARBOXYPHENYL-3-(6-OXOHYDROPURIN-9-YL) PROPANAMIDE ON GROWTH FACTOR mRNA LEVELS FOLLOWING SPINAL CORD HEMISECTION

To determine the effect of the administration of N-4-carboxyphenyl-3-(6-oxohydropurin-9-yl) propanamide on neurotrophic factor levels in the spinal cords of rats, the levels of such neurotrophic factors were measured under various conditions.

Methods

T8 Lesion Surgery

Male Wistar rats (250 g) anesthetized with ketamine/xylazine received either a partial laminectomy (sham operated control) or full laminectomy and unilateral transection of the spinal cord with a miniscalpel at the level of the eighth thoracic vertebrae. The animals were assigned into four groups: two control groups, one group receiving N-4-carboxyphenyl-3-(6-oxohydropurin-9-yl) propanamide (20 mg/kg day) in the drinking water and the other receiving no treatment. The two other groups were both lesion groups of untreated and treated with N-4-carboxyphenyl-3-(6-oxohydropurin-9-yl) propanamide. A lesion was judged successful by the complete loss of withdrawal reflex 24 hours post surgery. At the end of the treatment period the animals were euthanized and perfused with saline. A 2 cm segment of cord was taken around the laminectomy site, called the lesion sample. Samples were also taken 2 cm above and 2 cm below the lesion (rostral and caudal sections respectively). A diagram of the lesion regions is shown in FIG. 1.

RNA Extraction and RT-PCR

Total RNA was extracted from coded unfixed spinal tissue samples using TRIzol reagent (Gibco-BRL). Total RNA (3

μg) was reversed transcribed using a recombinant MMLV reverse transcriptase (RT) called Superscript II (Gibco-BRL) in a 20 μl reaction primed with oligo-dT$_{18}$ (MOBIX) using buffer and dithiothreitol supplied with the enzyme. Two aliquots (1 and 2.5 μl) of the RT mixture were amplified in a mixture containing 0.2 mM dNTPs, 1×PCR buffer, 1.5 mM MgCl$_2$, Taq polymerase (Gibco-BRL) and 0.1 μg of sense and antisense primer (MOBIX). The quantitation of products was done from ethidium bromide stained gels using an LKB laser scanner using the ratio of the 1 μl to 2.5 μl replicates to ensure that threshold fluorescence had not been reached. All samples were read in the exponential phase of the amplification curve for the primer set. All three primers sets were run from the same RT sample. The equivalence of the amount of RNA in each of the samples was corrected for the expression of the housekeeping gene, G3PDH.

Results

Figure 2:
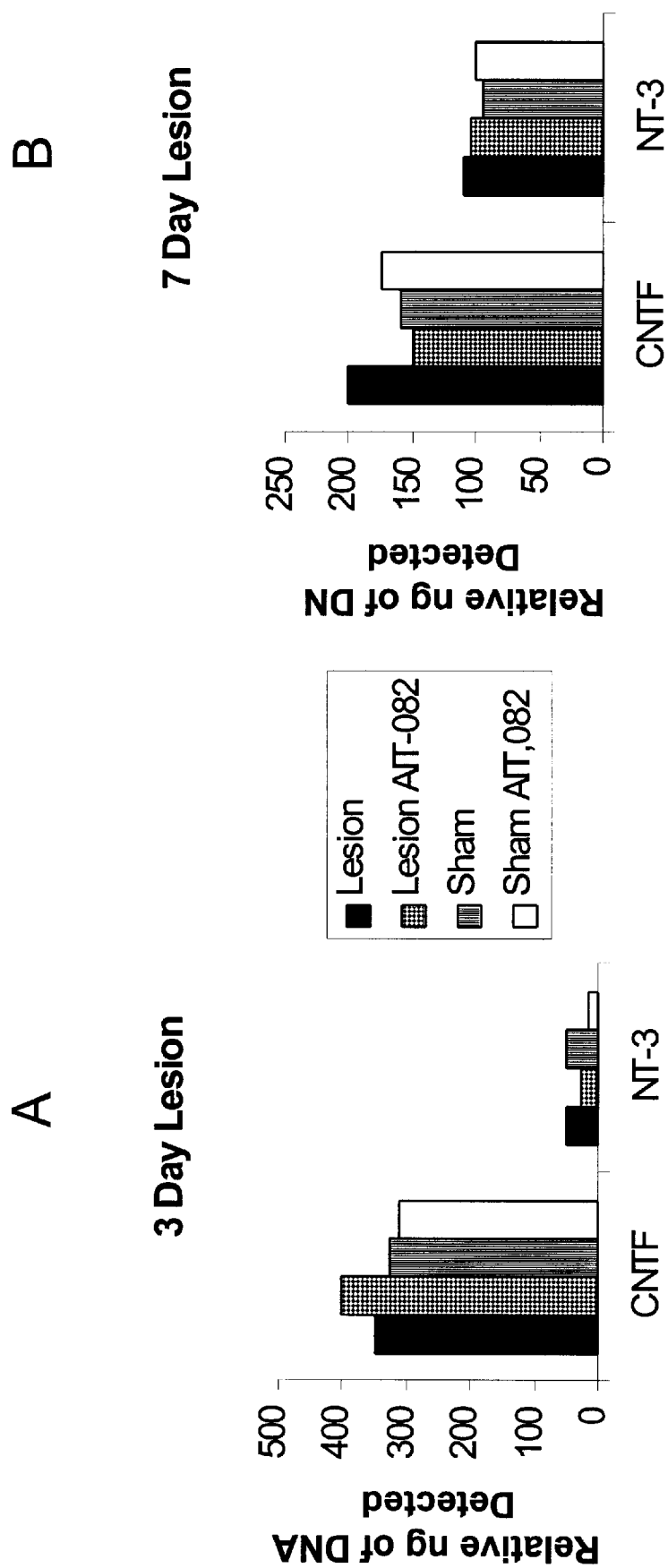
FIG. 2 is a graph of the level of mRNA for the neurotrophic factors brain-derived neurotrophic factor (BDNF), ciliary neurotrophic factor (CNTF), and NT-3 at the lesion site for animals lesioned or sham-lesioned in Example 1: (a) levels measured 3 days after lesioning or sham-lesioning; (b) levels measured 7 days after lesioning or sham-lesioning.
Figure 3:
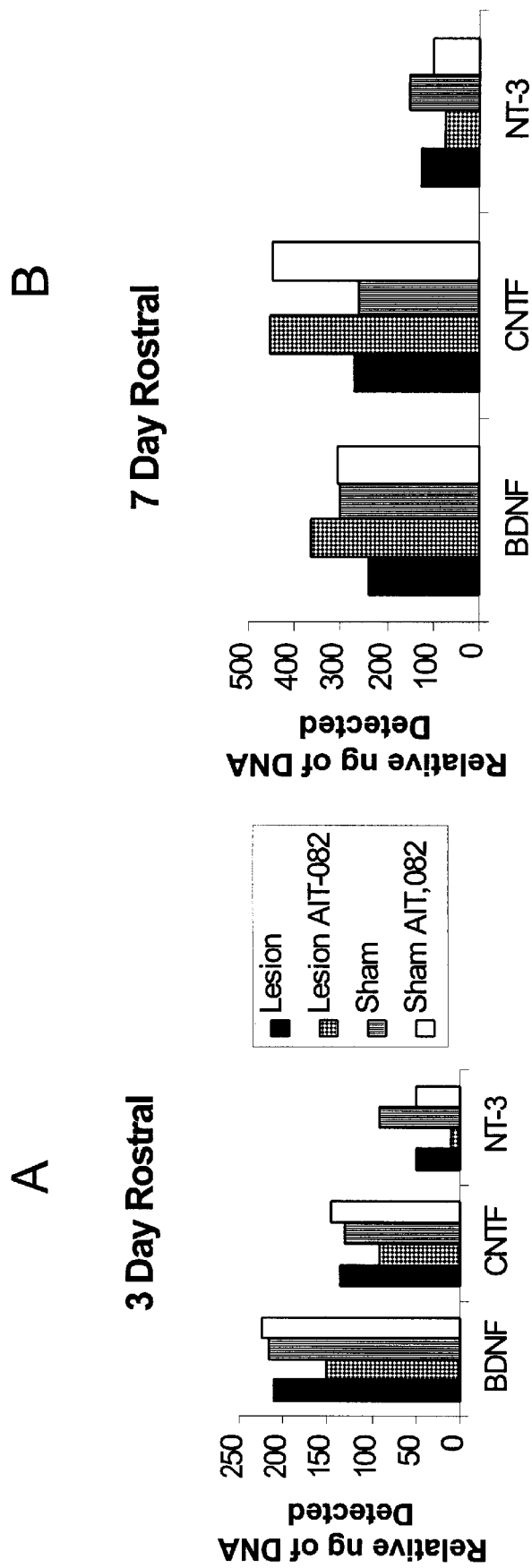
FIG. 3 is a graph of the levels of mRNA for BDNF, CNTF, and NT-3 rostral to the lesion for animals lesioned or sham-lesioned in Example 1:(a) levels measured 3 days after lesioning or sham-lesioning; (b) levels measured 7 days after lesioning or sham-lesioning.
Figure 4:
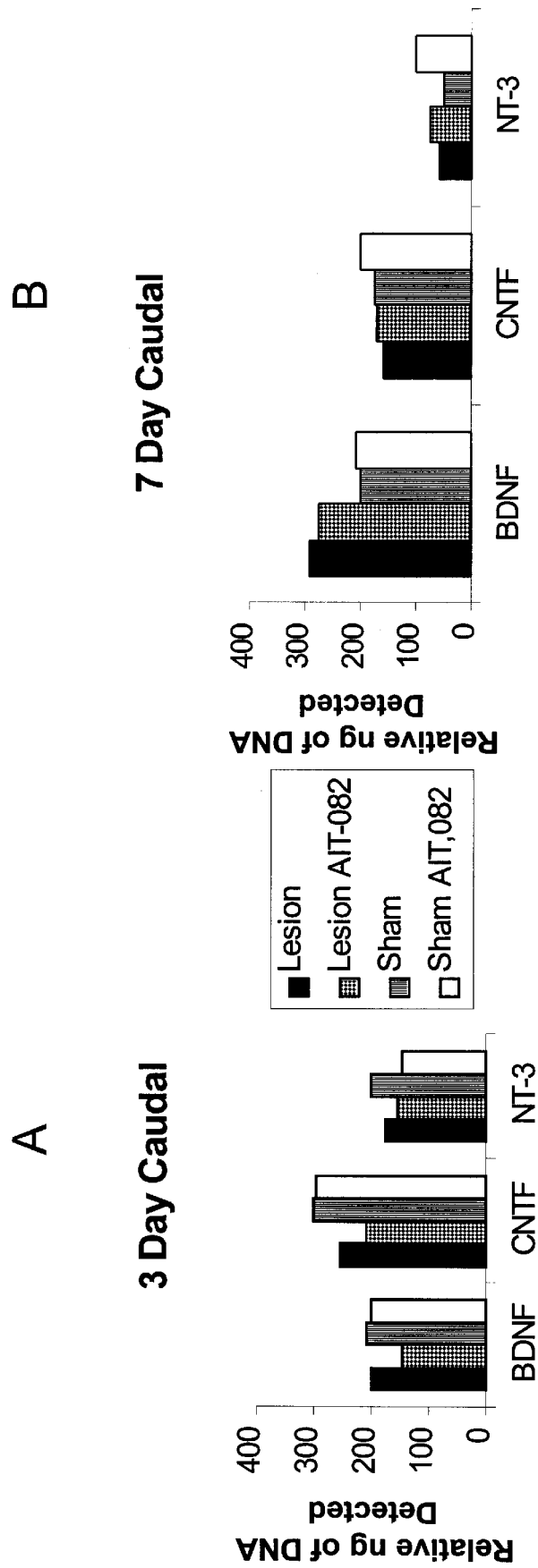
FIG. 4 is a graph of the levels of mRNA for BDNF, CNTF, and NT-3 caudal to the lesion for animals lesioned or sham-lesioned in Example 1:(a) levels measured 3 days after lesioning or sham-lesioning; (b) levels measured 7 days after lesioning or sham-lesioning.

RT-PCR was used to measure the mRNA levels of 3 neurotrophic factors, CNTF, BDNF, and NT-3 in 3 sections of the spinal cord as illustrated in FIGS. 2–4, after 3 or 7 days of treatment with N-4-carboxyphenyl-3-(6-oxohydropurin-9-yl) propanamide. The levels of gene expression were normalized to G3PDH expression. The results are expressed as relative ng of DNA after RT-PCR which are considered to reflect the levels of mRNA expression in the original RNA samples.

Rostral to the lesion, 3 days of treatment with N-4-carboxyphenyl-3-(6-oxohydropurin-9-yl) propanamide significantly increased the levels of BDNF and CNTF mRNA in sham-operated animals over the lesion animals. This trend was reversed for BDNF after 7 days of treatment with the compound when the relative levels of mRNA expression were significantly higher in the lesioned animals treated with the compound than in the lesioned animals that had not been treated with the compound. The compound, after 7 days, increased CNTF mRNA levels relative to lesion alone (p=0.056). However, in the control animals, the drug treatment induced a robust increase (p=0.017) in CNTF levels over water alone. At the rostral level, the surgical treatment alone did not significantly alter CNTF mRNA levels. At the level of the lesion, treatment with the compound increased mean CNTF mRNA levels over control animals, although not statistically so. There were no significant differences due to surgery or drug treatment at this level.

Caudal to the lesion for the control animals, NT-3 mRNA was decreased after 3 days of treatment with the compound. BDNF mRNA was higher in the sham-operated animals than in the lesioned animals when both groups received the compound. There were no significant effects with 7 days of treatment with the compound post surgery.

The levels of mRNA at the lesion site for the neurotrophins are shown in FIG. 2 (FIG. 2a, after 3 days of treatment; FIG. 2b, after 7 days of treatment). The animals were treated for 3 (FIG. 2a) or 7 days (FIG. 2b) as indicated. The error bars represent S.E.M. s (n=3 or 4). There were no significant differences between treatment groups. The mRNA levels shown in FIG. 2 were measured by RT-PCR on a 2 cm portion of the spinal cord at the T8 lesion site as described above.

The effects of the compound on levels of mRNA rostral to the lesion are shown in FIG. 3 (FIG. 3a, after 3 days of treatment; FIG. 3b, after 7 days of treatment). The animals were treated for 3 (FIG. 3a) or 7 days (FIG. 3b) as indicated. The mRNA levels were measured by RT-PCR on a 2 cm portion of the spinal cord 1 cm up from the T8 lesion site as described above. Statistical significance was determined by one-way Anova testing. Error bars represent S.E.M.s (n=3 or 4). The level of mRNA for CNTF in the sham-lesioned animals treated with the compound were significantly different from sham-lesioned animals treated only with water (p<0.05) after 7 days of treatment. The level of mRNA for BDNF was also significantly different when lesioned animals treated with the compound were compared with lesioned animals treated only with water (p<0.05) after 7 days of treatment. The level of BDNF mRNA after 3 days of treatment in control animals (i.e. sham-lesioned animals) treated with the compound was significantly different from lesioned animals treated with the compound (p<0.05). Finally, the level of CNTF mRNA at 3 days of treatment in control animals treated with the compound was again significantly different from lesioned animals treated with the compound (p<0.01).

The effects of the compound on levels of mRNA caudal to the lesion are shown in FIG. 4 (FIG. 4a, after 3 days of treatment; FIG. 4b, after 7 days of treatment). The mRNA levels were measured by RT-PCR on a 2 cm portion of the spinal cord 1 cm down from the T8 lesion site as indicated above. The animals were treated for 3 (FIG. 4a) or 7 days (FIG. 4b) as indicated. Statistical significance was determined by one-way Anova testing. Error bars represent S.E.M.s (n=3 or 4). The level of NT-3 mRNA was lower after treatment with the compound in sham-lesioned animals as compared with sham-lesioned animals not treated with the compound (p<0.05) after 3 days of treatment.

In conclusion, the compound appeared to suppress neuronal production of NT-3 at three days of treatment in the cords of control (sham-lesioned) animals. While the effect was significant only in the segment caudal to the lesion, the trend was seen in all three segments of the cord. Seven days of treatment with the compound resulted in increased CNTF in the cords of control animals, though statistical significance was seen only in one segment. BDNF was markedly elevated in lesioned animals treated with the compound in the cord rostral to the lesion. The elevated expression seen in this segment may reflect the increased population of neuronal cells that were present at this level of the cord.

ADVANTAGES OF THE PRESENT INVENTION

The present invention provides an efficient method for stimulating mammalian motor neuron regeneration. The method is particularly useful in circumstances in which injury or disease has led to degeneration of motor neurons. Because the method is likely to operate through endogenous stimulation of nerve growth factors, it is likely to be relatively free of side effects. The method of the present invention also can be used with other secondary treatments that reduce inflammation and edema. The present invention provides molecules that are able to cross the blood-brain barrier without the requirement of direct injection of the molecules into nervous tissue. The present invention also surmounts the difficulties typically associated with transplantation of transfected cells.

I claim:

1. A method of stimulating regeneration or survival of a mammalian motor neuron or a mammalian sensory neuron comprising administering to a mammal an effective amount of a compound of formula (I)

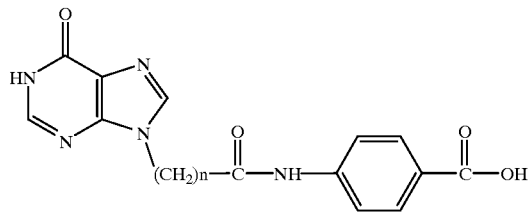

(I)

wherein n is an integer having the value 4, 5, or 6 or of a salt or prodrug ester of a compound of formula (I) wherein n is an integer having the value 4, 5, or 6.

2. The method of claim 1 wherein the compound is a compound of formula (I) wherein n is an integer having the value 4, 5, or 6.

3. The method of claim 2 wherein the administration of the compound of formula (I) increases the level of mRNA for at least one neurotrophic factor in a tissue that is in chemical communication with the motor neuron or the sensory neuron, the neurotrophic factor stimulating the growth of neurons.

4. The method of claim 3 wherein the neurotrophic factor is selected from the group consisting of nerve growth factor, NT-3, brain-derived neurotrophic factor (BDNF) and ciliary neurotrophic factor (CNTF).

5. The method of claim 4 wherein the neurotrophic factor is nerve growth factor.

6. The method of claim 4 wherein the neurotrophic factor is NT-3.

7. The method of claim 4 wherein the neurotrophic factor is brain-derived neurotrophic factor.

8. The method of claim 4 wherein the neurotrophic factor is ciliary neurotrophic factor.

9. The method of claim 1 wherein the neuron is a mammalian motor neuron.

10. The method of claim 1 wherein the neuron is a mammalian sensory neuron.

11. A pharmaceutical composition comprising:
   (a) an effective amount of compound of formula (I) wherein n is an integer having the value 4, 5, or 6 or of a salt or prodrug ester of a compound of formula (I) wherein n is an integer having the value 4, 5, or 6; and
   (b) a pharmaceutically acceptable carrier; wherein the compound is formulated for stimulation of regeneration or survival of a mammalian motor neuron or a mammalian sensory neuron.

12. The pharmaceutical composition of claim 11 wherein the composition comprises an effective amount of a compound of formula (I) where n is an integer having the value 4, 5, or 6.

* * * * *